(12) United States Patent
Bourne et al.

(10) Patent No.: US 7,947,021 B2
(45) Date of Patent: May 24, 2011

(54) ANTIMICROBIALLY-CHARGED ENTRY PORT CUFF

(75) Inventors: George Bourne, Southboro, MA (US); Robert Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2014 days.

(21) Appl. No.: 10/434,526

(22) Filed: May 8, 2003

(65) Prior Publication Data
US 2004/0225264 A1 Nov. 11, 2004

(51) Int. Cl.
*A61M 5/32* (2006.01)

(52) U.S. Cl. .................. 604/265; 604/268

(58) Field of Classification Search .......... 604/265, 604/20, 21, 500, 174, 177, 264, 268, 523, 604/541, 544, 322
See application file for complete search history.

(56) References Cited

U.S. PATENT DOCUMENTS

| | | | |
|---|---|---|---|
| 4,623,329 A | 11/1986 | Drobish et al. | 604/29 |
| 5,001,009 A | 3/1991 | Whitbourne | 428/412 |
| 5,049,140 A | 9/1991 | Brenner et al. | 604/266 |
| 5,236,422 A | 8/1993 | Eplett, Jr. | 604/265 |
| 5,344,411 A | 9/1994 | Domb et al. | 604/265 |
| 5,505,695 A * | 4/1996 | Eplett, Jr. | 604/544 |
| 5,520,664 A | 5/1996 | Bricault, Jr. et al. | 604/265 |
| 5,599,311 A | 2/1997 | Raulerson | 604/175 |
| 5,620,424 A * | 4/1997 | Abramson | 604/265 |
| 5,686,096 A | 11/1997 | Khan et al. | 424/443 |
| 5,820,607 A | 10/1998 | Tcholakian et al. | 604/265 |
| 6,168,580 B1 | 1/2001 | Yardley | 604/265 |
| 6,387,080 B1 | 5/2002 | Rødsten | 604/265 |
| 6,402,735 B1 * | 6/2002 | Langevin | 604/523 |
| 6,700,032 B1 * | 3/2004 | Gray | 602/48 |

OTHER PUBLICATIONS

Hanna et al., *New Approaches for Prevention of Intravascular Catheter-Related Infections*, Infect Med 18(1):38-48, 2001, at http://www.medscape.com.

Lin et al., *Prevention of shunt infections in an animal model using iodine-impregnanted catheters*, Child's Nervous System 16(8):536, 2000.

* cited by examiner

*Primary Examiner* — Nicholas D Lucchesi
*Assistant Examiner* — Laura A Bouchelle
(74) *Attorney, Agent, or Firm* — Mayer & Williams PC; David B. Bonham; Keum J. Park

(57) ABSTRACT

An entry port cuff for providing antimicrobial properties to a medical device having a portion that is insertable into the body of a patient is disclosed. The cuff, which is charged with an antimicrobial agent, is removably attached to the medical device immediately prior to or immediately after insertion of said medical device into the body. The cuff is attached to the medical device in a manner such that the cuff is located outside of the body and in the proximity of the point of entry of the medical device into the body. Also, the cuff is substantially free of an adhesive for adhering the cuff to the body. Methods for using and making the entry port cuff are also described.

7 Claims, 4 Drawing Sheets

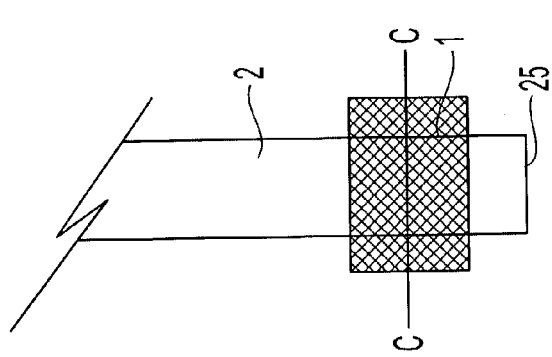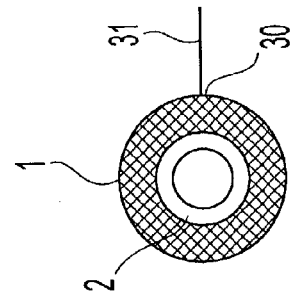
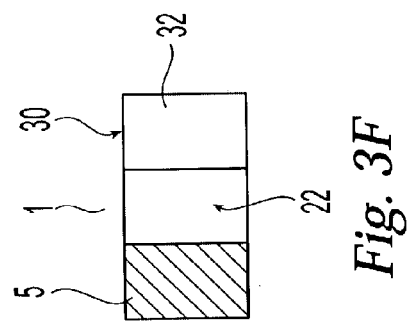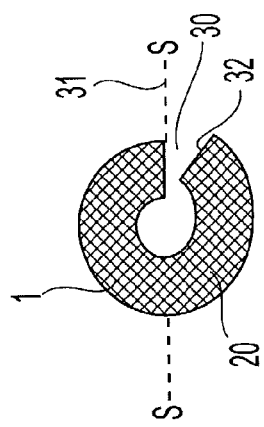
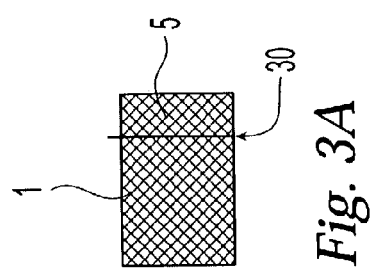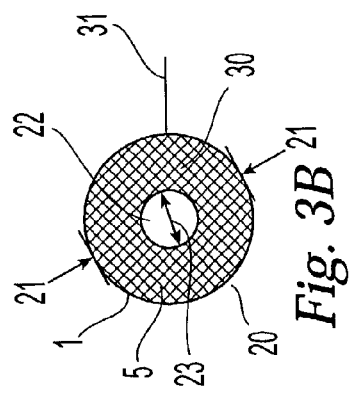

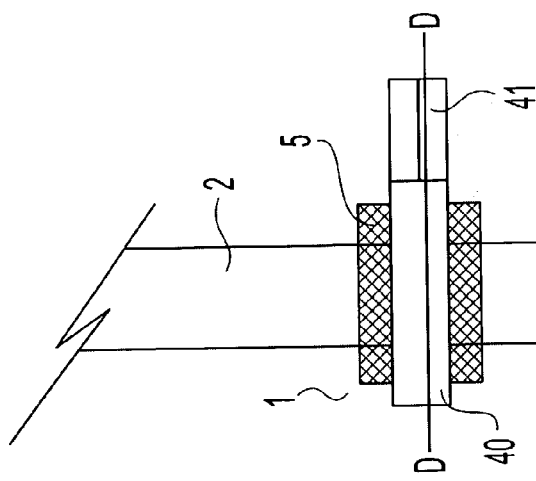
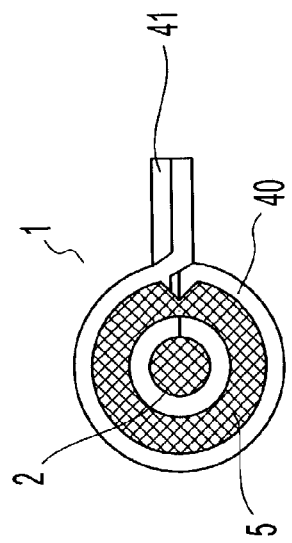
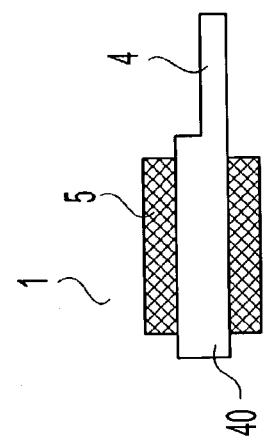
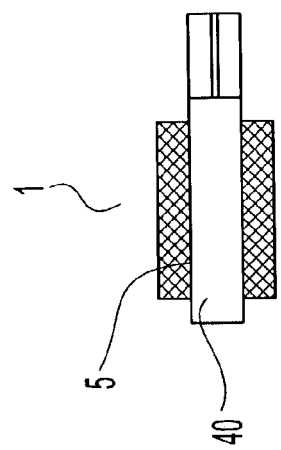
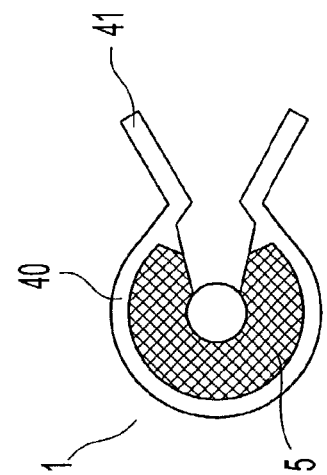
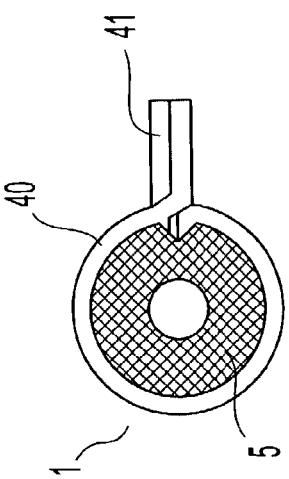
Fig. 4A
Fig. 4B
Fig. 4C
Fig. 4D
Fig. 4E
Fig. 4F

ANTIMICROBIALLY-CHARGED ENTRY PORT CUFF

FIELD OF THE INVENTION

This invention relates generally to medical devices and methods for preventing microbial infection while using medical devices that are inserted or implanted into the body of a patient. More particularly, the invention is directed to an entry port cuff that can be removably attached to a medical device immediately before or immediately after insertion of the medical device into the patient's body. While in use, the cuff is located outside the body and in the proximity of the point of entry of the medical device into the body of the patient.

BACKGROUND OF THE INVENTION

The use of implanted medical devices, while critical to many treatment modalities, is associated with undesirable infections. Approximately 60,000 deaths in the United States occur annually from device-related, hospital-acquired (nosocomial) infections. In the United States, bacterial infections from medical devices cause 9 to 11 million infections and 87,500 to 350,000 deaths per year. Urinary catheters alone cause more than 500,000 urinary tract infections per year. A 10-year study by the Centers for Disease Control (CDC) found a 7% incidence of nosocomial infections among all U.S. hospital admissions and even higher rates internationally. Each year, there are an estimated 2 million nosocomial infections in the United States and an estimated 3 million in Europe.

Many current infection control methods rely upon the use of antibiotics; however, these methods are problematic due to the natural ability of many microbes to develop resistance against existing antibiotics. According to the CDC, the "last line of antibiotic defense has been breached." Therefore, there exists a need for effective non-antibiotic infection control technologies to reduce the estimated $6.5 billion annual cost associated with nosocomial infections in the United States. There is great a need to prevent infection resulting from the use of medical devices that are inserted into the body of a patient, such as devices used for localized delivery of biologically active materials to the body of a patient, or during intravenous delivery of fluids or medications to the body of a patient. Patients that will benefit the most from such devices and methods for their use are those at the highest risk for blood infection and death.

A number of devices are available in the art for providing an antimicrobial environment or antimicrobial properties for insertable medical devices. Currently there are present in the art various patents describing medical devices whose surfaces can be covered with antimicrobial agents. For example, U.S. Pat. No. 5,344,411 to Domb et al. discloses an anti-infective coating bound to the surface of a catheter or other medical device. The catheter is coated with solutions of an antimicrobial agent and water and is allowed to dry. The water on the catheter then evaporates, leaving an anti-infective coating on its surface. What remains is a medical device whose surface is left directly coated with an antimicrobial agent.

Also in the art are various coating compositions and methods for coating medical devices. For example, U.S. Pat. No. 5,001,009 to Whitbourne discloses a method for coating a substrate such as a medical device with coatings, comprising applying each solution to the substrate surface and then evaporating it at an elevated temperature. In U.S. Pat. No. 6,387,080 to Rodsten discloses a method for forming an osmolality promoting hydrophilic coating on the surface of a medical device such as a catheter.

However, medical devices whose surfaces are charged or coated with antimicrobial agents can exhibit a risk of leeching, leaking and migration of the antimicrobial agent away from the portion of the device that requires the antimicrobial agent. The terms "leeching," "leaking" and "migration" are used to describe the movement of the antimicrobial agent away from a portion of the medical device that should include the antimicrobial agent. One of the portions of the medical device that requires an antimicrobial agent is the portion that is located in proximity of the point of entry of the medical device into the patient's body. It is desirable for an antimicrobial agent to be located in the proximity of the point of entry of the medical device so that microbes that can cause infections can be killed off or prevented from entering the body. Leeching, leaking or migration of the antimicrobial agent can lead to a reduced concentration of the antimicrobial agent in the portion of the medical device that is in proximity to the point of entry of the medical device. Therefore, there is a risk of diminished antimicrobial effect at the point where such an effect is needed the most. Such reduction in effectiveness results in a higher risk of infection, as well as higher costs and an unnecessary waste of antimicrobial agents.

Therefore, it has been found that the amount of antimicrobial can be used most efficiently if it is somehow concentrated at the point where it can be the most useful for preventing infection. U.S. Pat. No. 5,049,140 to Brenner et al. discloses a catheter with an antimicrobial fitting that can be cut into a plurality of pieces and attached at fixed distances along the length of the catheter. The fittings are fabricated from a heavy rubber elastomer (with a Shore A hardness of between 80 and 95) and are fixed permanently onto the length of the catheter.

U.S. Pat. Nos. 5,236,422 and 5,505,695 to Eplett describe cuffs for urinary catheters, wherein only the cuffs themselves are charged with an antimicrobial agent. These cuffs are inserted into the body of the patient (through the urethra) as a means for preventing infection from bacteria migrating along the length of a urinary catheter inside the body of the patient. However, these cuffs are fully inserted into the body of the patient, rather than being attached on the device at a point external to and proximate of the point of entry of the medical device. The cuffs described in those two patents are placed completely inside the urethra, and their antimicrobial effect is concentrated at the internal point of insertion of the catheter into the patient's body. There are drawbacks to putting the cuff into the body of the patient. Locating the cuff completely inside the body is not desirable because it may expose internal body tissues to infection. It is also often more painful for the patient, and may require a larger incision and therefore a heightened likelihood of infection at the point of entry.

Also present in the art are devices, such as those described in U.S. Pat. No. 5,686,096 to Khan et al., in which an antimicrobially charged device comprises a resilient pad that is attached to the skin of the patient. The pad, which contains an antimicrobial agent, has at least one void for receiving a catheter. The pad is affixed to the skin of the patient by the use of an adhesive. Such adhesives are a drawback because they can irritate the skin.

Therefore, there is a need for medical devices or components of medical devices that can provide adequate antimicrobial protection from infections and that also avoid leaking or migration of the antimicrobial agent from the portion of the medical device that should include the antimicrobial agent.

SUMMARY OF THE INVENTION

To achieve the aforementioned objectives, we have invented a removable entry port cuff that comprises an antimicrobial agent. The cuff is removably attached to a medical device and can be used to provide antimicrobial properties to a medical device such as a catheter immediately prior to or immediately after insertion of the device into the body of a patient. This results in an effective delivery of an antimicrobial agent to a patient to prevent infection while avoiding the undesired migration or leaking of the antimicrobial agent from the portion of the medical device that is located external to and in proximity to the point of entry of the medical device into the body.

In particular, the invention is directed to an entry port cuff that provides an antimicrobial properties to a medical device having a portion that is insertable into the body of a patient. The cuff comprises a polymeric material charged with the antimicrobial agent, and the cuff is substantially free of an adhesive for adhering the cuff to the body of the patient. Furthermore, the cuff is removably attached to the medical device immediately prior to or immediately after insertion of the medical device into the body. The cuff is attached to the medical device in a manner such that the cuff is located outside of the body and in the proximity of the point of entry of the medical device into the body.

Also, the cuff can be separately packaged from the medical device prior to attachment of the cuff to the medical device. Moreover, the polymeric material of the cuff can be charged with the antimicrobial agent prior to the cuff being packaged. Alternatively, the polymeric material of the cuff that is separately packaged can be charged with the antimicrobial agent immediately prior to attachment of the cuff to the medical device. In certain embodiments, the polymeric material of the cuff is a polyurethane foam or a latex. Additionally, the polymeric material of the cuff comprises a split therein to facilitate attachment of the cuff to the medical device. Also to facilitate attachment of the cuff to the medical device, the cuff can further comprise a spreader having tabs that is attached to the polymeric material.

Moreover, the invention is directed to a method of preventing microbial infection resulting from the insertion into the body of a patient of a medical device. In this method, a cuff comprising a polymeric material charged with an antimicrobial agent is obtained. The cuff can be substantially free of an adhesive for adhering the cuff to the patient's body. Furthermore, the cuff is removably attached to the medical device immediately prior to or immediately after insertion of the medical device in the body. The cuff is attached in a manner such that the cuff is located outside the body and in the proximity of the point of entry of the medical device into the body.

BRIEF DESCRIPTION OF THE DRAWINGS

FIG. 11B shows the medical device with the cuff when the medical device is inserted into the body of a patient.

FIGS. 3A-3E show an embodiment of a cuff of the invention having a split therein.

FIGS. 4A-4E show an embodiment of a cuff of the invention having a spreader with tabs for assisting the attachment of the cuff onto a medical device.

DESCRIPTION OF THE PREFERRED EMBODIMENTS

Figure 1A:
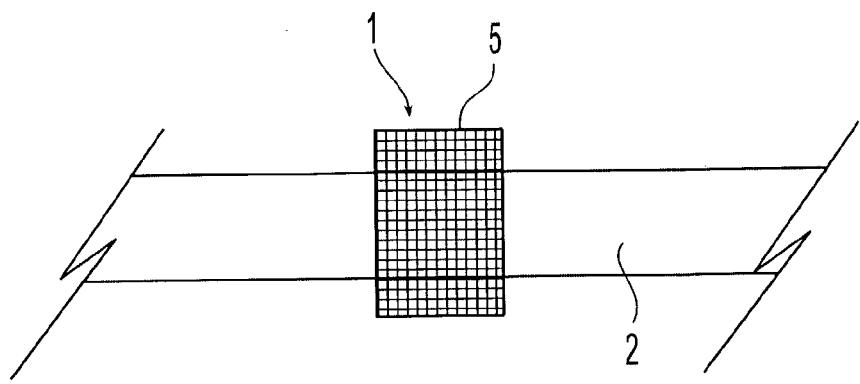
FIG. 1A shows a cuff of the invention attached to a portion of a medical device.
Figure 2E:
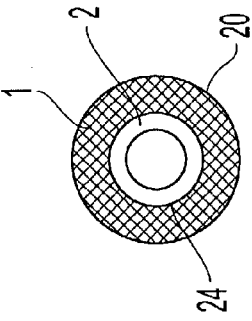
FIGS. 2E-2F show a perspective view of the cuff attached to the medical device and a cross-sectional thereof, respectively.
Figure 2F:
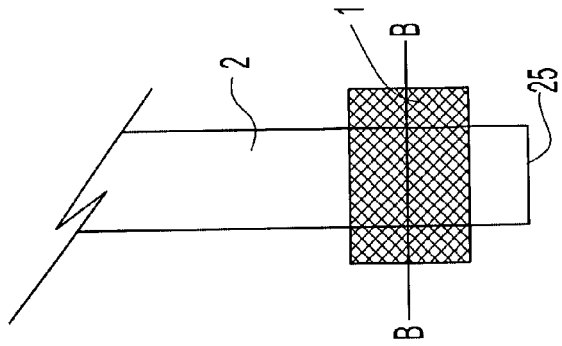
Figure 2C:
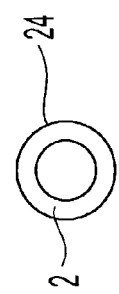
FIGS. 2C-2D show a perspective view of a medical device and a cross-section of the medical device, respectively.
Figure 2D:
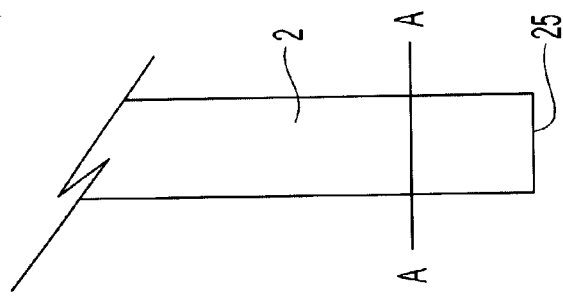

FIG. 1A illustrates an embodiment of the invention. The embodiment comprises a cuff 1 made of a polymeric material 5 such as a foam. The term "cuff" is defined as any sleeve, sheath or fitting through which the medical device can be inserted for a snug or tight fit. As shown in FIG. 2B, which is a top view of the cuff 1, the polymeric material 5 that makes up the cuff 1 will generally be in a ring-like shape having an outer surface 20 and an outer diameter 21. The opening 22 in the polymeric material 5 of the cuff 1 has an inner diameter 23. Although the opening 22 is shown as a circular hole, the opening 22 can have other shapes as well.

Referring again to FIG. 1A, the cuff 1 is removably attached to a medical device 2, i.e. the cuff 1 can be removed after it is attached to the medical device 2. The cuff 1 can be attached immediately prior to or immediately after the insertion of the medical device 2 into the body of the patient. The term "immediately prior to" means within an hour before attachment of the cuff to the medical device. The term "immediately after" means within 1 hour after attachment of the cuff to the medical device. By attaching the cuff onto the medical device immediately before or after insertion of the medical device into the body minimizes the possibility that the antimicrobial agent will leak or migrate from the point of entry of the device.

Figure 1B:
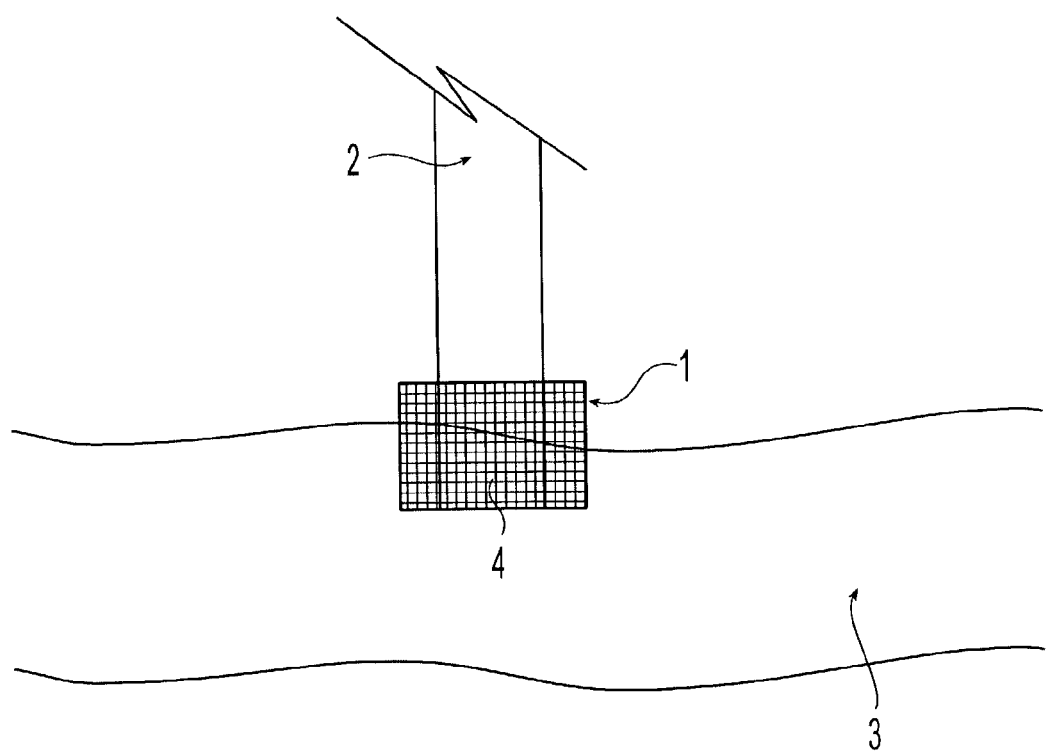

FIG. 1B illustrates the medical device 2 with the cuff 1 attached thereon, while the medical device 2 is inserted into the body of the patient 3. The cuff 1 remains outside the body of the patient 3 when the medical device is inserted into the body. Furthermore, the cuff 1 is located in the proximity or near the point of entry 4 of the medical device 2 into the body of the patient 3 to provide an antimicrobial effect at the point of entry 4.

The terms "point of entry" or "entry port" are defined as the point of penetration on the surface of the skin of the patient at which the medical device is inserted. When removably attached, the cuff of the present invention remains outside of the patient's body at all times, but in the proximity of the point of entry. The term "proximity of the point of entry" is defined as sufficiently close to the point of entry such that the cuff will provide an antimicrobial effect at the point of entry. Preferably, the cuff surrounds the point of entry of the device or is in direct contact with the point of entry.

Figure 2A:
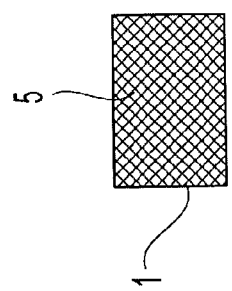
FIGS. 2A-2B show a cuff of the invention that is not yet attached to a medical device.
Figure 2B:
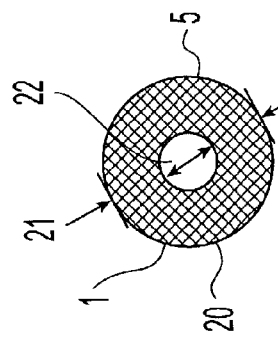

FIG. 2A illustrates a side view of the cuff 1 of the invention before it is attached to the medical device 2. FIG. 2B illustrates the top view of the cuff 1. As shown in FIG. 2B, the polymeric material 5 of the cuff 1 in this embodiment has an outer surface 20 having a circular circumference. The outer surface 20 need not have a circular circumference, but instead can be in a variety of shapes, e.g., square or triangular circumference.

FIG. 2C shows a portion of a medical device 2, such as a catheter. FIG. 2D shows a cross-sectional view of the medical device 2 along lines A-A of FIG. 2C. The medical device has an outer diameter 24.

FIG. 2E shows the cuff 1 in FIGS. 2A and 2B when it is attached to the medical device 2. FIG. 2F shows a cross-sectional view of the cuff 1 attached to the medical device 2 along line B-B of FIG. 2E. In this embodiment, the cuff 1 is attached to the medical device 2 by inserting an end 25 of the medical device 2 into the opening 22 of the cuff 1. The cuff 1 is then moved along the medical device 2, e.g., by sliding it, until it reaches the desired point on the medical device 2. The opening 22 preferably has a diameter 23 that is smaller than the outer diameter 24 of the portion of the medical device 2 onto which the cuff 1 is to be attached. Because the diameter 23 of the opening 22 of the cuff 1 is smaller than the outer diameter 24 of the portion of the medical device 2 onto which the cuff 1 is to be attached, the cuff 1 fits snugly around the medical device 2 as shown in FIG. 2F. The snug fit ensures that the cuff and medical device will not shift with respect to each other so that the maximum amount of antimicrobial agent can be delivered to or near the point of entry of the medical device. Furthermore, because of the snug fit between the cuff and the medical device, there is no need for the use of an adhesive for adhering the cuff to the body of the patient to prevent the shifting of the cuff. Avoiding the use of such adhesive is desirable because application of the adhesive to the patient's skin can irritate the skin and result in other adverse effects, such as lack of compatibility between the antimicrobial agents used and the adhesives.

FIG. 3A shows a side view of a cuff 1 of the invention and FIG. 3B shows a top view of the cuff 1. The cuff 1 has a split 30 that extends: (1) between the opening 22 and the outer surface 20 of the polymeric material 5 of the cuff 1 (as shown in FIG. 3B) and (2) through the entire thickness of the cuff 1 (as shown in FIG. 3A). The split 30 allows the cuff 1 to be opened, as shown in FIG. 3C, so that the cuff 1 can be readily placed around or attached to the medical device 2 (as shown in FIG. 3D). When the cuff 1 is attached to the medical device 2, the split 30 will close or will become sealed as shown in FIG. 3E, which is a cross-sectional view of the cuff 1 attached to the medical device 2 along line C-C in FIG. 3D. Since the diameter 23 of the opening 22 of the cuff 1 is smaller that the outer diameter of the medical device 2, the cuff 1 fits snugly around the medical device 2. When the cuff 1 has a split 30, the cuff can be attached to the medical device either immediately before or after the medical device 2 is implanted into the body.

In addition, an adhesive can be used to seal the split. FIG. 3F shows a view of FIG. 3C along line S-S. An adhesive is placed on at least one surface 32 of the split 30 to assist the sealing of the split 30 when the cuff 1 is attached to the medical device 2. For instance, as shown in FIG. 3C, an adhesive paper comprising a piece of release paper 31 and an adhesive applied to one surface of the release paper 31 can be placed at the surfaces 32 of the split 30. The adhesive is placed against the surface 32 of the split 30. After the cuff 1 is attached to the desired location of the medical device 2, the release paper 31 is removed. The surfaces 32 of the split 30 are then squeezed together to seal the split 30.

FIG. 4A shows a side view of another embodiment of the cuff 1 of the invention. FIG. 4B shows a top view of this cuff 1 before it is attached to the medical device 2. The cuff 1 comprises a polymeric material 5 having a ring-like shape. This polymeric material 5 is attached to a spreader 40, which has a ring-like shape with an opening. The spreader 40 comprises tabs 41 located at the opening of the spreader 40. The spreader 40 can be in an opened position (see FIG. 4C, which is a side view of the cuff and FIG. 4D, which is a top view of the cuff in an opened position) or a closed position (FIG. 4B). As shown in FIG. 4D, the cuff 1 can be opened by pulling apart the tabs 41 of the spreader 40. When the cuff 1 is opened, it is in a relaxed position (FIG. 4D). The cuff 1 can then be placed around the medical device 2 as shown in FIG. 4E. The tabs 41 are then squeezed together to close the cuff 1 as in FIG. 4F, which is a cross-sectional view along line D-D of FIG. 4E. The tabs 41 can close or lock in place when they are snapped together as shown in FIG. 4F. The skilled artisan is aware of other methods for closing the cuff 1. There are various other methods for closing the cuffs, including higher-cost methods such as magnetic means.

The cuff of the present invention can be used with any medical device capable of being inserted or implanted into the body of a patient. These devices include devices for treating blood vessels, the urinary tract, coronary vasculature, the esophagus, the trachea, the colon, and the biliary tract. Such devices include without limitation catheters, tracheotomy tubes, wound drains and any other type of intravenous tube. The medical device can be made from a variety of materials, preferably the device is made from polymer, such as polyethylene, polyamides, polyimides, PEBAX or similar material commonly in use in manufacturing such devices.

Also, the cuff of the present invention can be made from a number of appropriate absorbent materials. Preferred materials are polyurethane foam and other foam materials that are lightweight and sponge-like and can be easily formed into cuffs and attached and removed from medical devices. Latex can also be used. Generally any open cell foam material is acceptable.

The shape of the polymeric material used to make the cuff can be of any shape as long as it includes an opening or aperature into which the medical device can be inserted. Preferably, the opening is round. Also, the diameter of the opening should be equal to or slight smaller than the outer diameter of the portion of the medical device onto which the cuff is to be attached to ensure a snug fit.

The antimicrobial agents that are suitable for the present invention may be any antimicrobial agent commonly used in the field. One preferred antimicrobial agent is iodine. J. Lin et al., "Prevention of Shunt Infections in an Animal Model Using Iodine-Impregnated Catheters, "*Child's Nervous System*, Vol. 16(8), p. 536 (August 2000).

The cuff of the present invention is made by first selecting an appropriate polymeric material for the cuff. This material is then shaped into a ring-like shape or cuff. One of skill in the art is aware of methods of shaping the polymeric material into such a shape. Some examples are molding or die cutting into the desired shape. Thereafter, the polymeric material can be charged with the antimicrobial agent by dipping the material into a solution of the antimicrobial agent. One of skill in the art is aware of other methods for charging the material.

In one embodiment of the present invention, after the polymeric material is shaped into a cuff, the material can be charged with an antimicrobial agent and then packaged separately from the medical device prior to attachment of the cuff to the medical device. When it is time for the cuff to be attached to the medical device, the cuff can be unpackaged and thereafter attached to the device. Such separate packaging of the cuff from the medical device minimizes chances that the antimicrobial agent will leak or migrate from the portion of the medical device that will be in proximity to the point of entry of the medical device. Alternatively, the cuff may be packaged without charging the polymeric material with the antimicrobial agent. When it is time to attach the cuff to the medical device, the cuff can be unpackaged and then charged with the antimicrobial agent before the cuff is attached to the medical device. Preferably, the cuff is charged immediately before attachment to the medical device, i.e. within 1 hour before attachment. This embodiment also avoids the problems of leaking and migration of the antimicrobial agent, thereby maximizing the concentration of the antimicrobial agent at the point of entry of the medical device.

It will be appreciated by those skilled in the art that while the invention has been described above in connection with particular embodiments, the invention is not necessarily so limited and that numerous other embodiments, examples, uses, modifications and departures from the embodiments

We claim:

1. An entry port cuff for providing antimicrobial properties to a medical device having a portion that is insertable into the body of a patient, wherein the cuff comprises a polymeric material charged with an antimicrobial agent, and wherein the cuff is removably attached to the medical device such that the cuff is located outside of the body and will remain outside of the body and in proximity to the point of insertion into the body at all times after insertion into the body, and wherein the cuff is substantially free of an adhesive for adhering the cuff to the body, wherein the polymeric material comprises a split therein to facilitate attachment of the cuff to the medical device, and wherein the cuff further comprises a spreader having tabs, wherein the spreader is attached to the polymeric material.

2. A method of preventing microbial infection resulting from the insertion into the body of a patient of a medical device, comprising the steps of:
 (1) obtaining a cuff comprising a polymeric material charged with an antimicrobial agent, wherein the cuff is substantially free of an adhesive for adhering the cuff to the patient's body; and
 (2) removably attaching said cuff to the medical device immediately prior to or immediately after insertion of the medical device in the body, wherein the cuff is attached in a manner such that the cuff is located outside the body and in the proximity of the point of entry of the medical device into the body, and remains outside of the body and in proximity to the point of insertion into the body at all times after insertion into the body.

3. The method of claim 2, wherein the polymeric material is charged with the antimicrobial agent immediately prior to attaching the cuff to the medical device.

4. The method of claim 2, wherein the polymeric material comprises a polyurethane foam.

5. The method of claim 2, wherein the polymeric material comprises latex.

6. The method of claim 2, wherein the polymeric material comprises a split therein to facilitate attachment of the cuff to the medical device.

7. The method of claim 6, wherein the cuff further comprises a spreader having tabs, wherein the spreader is attached to the polymeric material.

* * * * *